(12) United States Patent
Morick et al.

(10) Patent No.: US 7,611,736 B2
(45) Date of Patent: Nov. 3, 2009

(54) PHARMACEUTICAL COMPOSITION FOR USE AS A LAXATIVE

(75) Inventors: Wolfgang Morick, Staufen (DE); Lars-Norbert Prenner, Bonn (DE); Michael Hubbert, Cologne (DE); Kurt Gebhart, Cologne (DE); Wolf Behm, Swisttal (DE)

(73) Assignee: Madaus GmbH, Cologne (DE)

( * ) Notice: Subject to any disclaimer, the term of this patent is extended or adjusted under 35 U.S.C. 154(b) by 0 days.

(21) Appl. No.: 12/420,602

(22) Filed: Apr. 8, 2009

(65) Prior Publication Data

US 2009/0186106 A1    Jul. 23, 2009

Related U.S. Application Data

(63) Continuation of application No. 12/140,102, filed on Jun. 16, 2008, and a continuation of application No. 12/040,290, filed on Feb. 29, 2008.

(30) Foreign Application Priority Data

May 2, 2007    (DE) .................. 10 2007 020 842
May 18, 2007   (DE) .................. 10 2007 023 397

(51) Int. Cl.
   *A61K 36/68*    (2006.01)
   *A61K 36/00*    (2006.01)

(52) U.S. Cl. .............. 424/738; 424/725; 424/776; 424/777

(58) Field of Classification Search ........ None
   See application file for complete search history.

(56) References Cited

U.S. PATENT DOCUMENTS

| | | | |
|---|---|---|---|
| 2,278,464 A * | 4/1942 | Musher | ............. 424/738 |
| 4,511,561 A | 4/1985 | Madaus | |
| 5,173,296 A | 12/1992 | Andre et al. | |
| 5,232,698 A | 8/1993 | Hord | |
| 5,232,699 A | 8/1993 | Colliopoulos | |
| 5,258,181 A | 11/1993 | Creiger et al. | |
| 5,320,847 A | 6/1994 | Valentine et al. | |
| 5,340,580 A | 8/1994 | Barbera | |
| 6,709,678 B2 * | 3/2004 | Gruber | ............. 424/490 |
| 2004/0009234 A1 | 1/2004 | Meisel et al. | |
| 2005/0053676 A1 | 3/2005 | Schata et al. | |
| 2005/0129781 A1 | 6/2005 | Skiendzielewski et al. | |
| 2008/0008741 A1 * | 1/2008 | Raz et al. | ............. 424/439 |

FOREIGN PATENT DOCUMENTS

| | | | |
|---|---|---|---|
| FR | 2646352 | | 11/1990 |
| GB | 2067402 | * | 7/1981 |
| RU | 2 134 044 | | 8/1999 |
| RU | 2 264 223 | | 8/1999 |
| WO | WO2007/013093 | | 2/2007 |

OTHER PUBLICATIONS

Bossi et al. Acta Bio-Medica de l'Ateneo Permense. 1986. vol. 57, No. 5-6, pp. 179-186, BIOSIS Abstract.*
Ewe et al. Pharmacology. 1993. vol. 47 (S1), pp. 242-248, CAPLUS Abstract.*
72 Fed. Reg. 60, 14669-74 (Mar. 29, 2007).

* cited by examiner

*Primary Examiner*—Christopher R. Tate
(74) *Attorney, Agent, or Firm*—Alston & Bird LLP (57) ABSTRACT

The invention relates to a pharmaceutical composition which is suitable in particular for use as purgative (cathartic), where the composition comprises in combination and in each case in pharmaceutically effective amounts (A) senna fruit dry extract and (B) *plantago* seeds (plantaginis ovatae semen). The composition can advantageously be manufactured by fluidized bed granulation. The composition is in particular free of guar gum, is dust-free, is dispersible in water and has a pleasant taste and can be supplemented straightforwardly with vitamins, minerals, trace elements and the like.

20 Claims, 4 Drawing Sheets

PHARMACEUTICAL COMPOSITION FOR USE AS A LAXATIVE

CROSS REFERENCES TO RELATED APPLICATIONS

This application is a continuation application of and claims priority from U.S. application Ser. No. 12/140,102 filed on Jun. 16, 2008, which in turn claims priority from U.S. application Ser. No. 12/040,290 filed Feb. 29, 2008, which in turn claims priority from German Patent Application No. DE 10 2007 020 842.3, filed May 2, 2007, and German Patent Application No. DE 10 2007 023 397.5, filed May 18, 2007, each entitled "NEW PHARMACEUTICAL COMPOSITION FOR USE AS A LAXATIVE". All priority references are expressly incorporated by reference herein, in their entirety.

BACKGROUND OF THE PRESENT INVENTION

The present invention relates to a novel composition, in particular pharmaceutical composition, for use as laxative (also referred to synonymously as "cathartic" or "purgative") and to a method for its manufacture, and to the use of this composition as laxative (i.e. cathartic or purgative).

Laxatives—also referred to synonymously as "purgatives" or "cathartics"—exist in very diverse forms, including numerous herbal cathartics.

Thus, for example, the use of *plantago* seed (plantaginis ovatae semen or semen plantaginis ovatae, also called synonymously Indian plantain, Indian psyllium, blond psyllium, ispaghula or semen ispaghulae) and/or its seed husks (*plantago* seed husks, plantaginis ovatae seminis integumentum) for medicaments for regulating bowel activity is known. *Plantago* seed has a considerable swelling ability and exerts a physical expansion stimulus on the sensitive receptors of the bowel walls. In a known method (cf. German patent 11 03 520), the seeds are finely ground, made into a viscous paste with water and dried in strand form, comminuted and finally coated.

The effect of the senna plant (senna plant, *Cassia senna* L. and *Cassia angustifolia* Vahl), especially its fruits (fructus sennae, also referred to synonymously as senna pods) (e.g. Alexandria senna fruits=sennae fructus acutifoliae and/or Tinnevelly senna fruits=sennae fructus angustifoliae) and their fruit husks as well as their leaves (folia sennae), as herbal cathartic is likewise known.

Laxatives which combine the two aforementioned action principles are also known, for example laxatives in which the physical effect of *plantago* seeds is supported by the pharmacologically stimulating action principle of the sennosides, the constituents of senna fruits, in order to achieve a better overall effect.

Thus, mixtures of ground *plantago* seeds and senna fruits as a simple mixture in which the constituents are present side by side have previously been disclosed. However, the flowability and suspendability in water cannot be optimally adjusted with such mixtures, but this would be desirable for oral administration. Processing of these mixtures to powders ready for administration is moreover impossible or not directly possible.

In order to remedy the aforementioned disadvantages, DE 30 01 357 C2 proposed a laxative in the form of cathartic granules based on senna fruits, *plantago* seeds and, where appropriate, *plantago* seed husks with an increased release-slowing effect, where the senna particles are enveloped or encased by *plantago* seeds, especially gummy substances of the *plantago* seeds. The composition described therein is an efficient laxative. However, since the composition is in the form of granules with a particle size of about 1 mm to about 3 mm of the granule particles, i.e. of asymmetric aggregates of powder particles, it must be taken with copious water. Otherwise there is the risk on inappropriate oral intake or administration, i.e. on oral intake or administration with amounts of water which are too small, that swollen lumps of the granules may form and may, in the worst cases, lead to blockage of the esophagus or else even of the gastrointestinal tract.

Laxatives which are based on plantains or Indian plantains (psyllium) or their constituents and which are on the market often do not have a sufficient cathartic effect and, after suspension in water, because of the rapid onset of the swelling effect of the plantain, do not remain drinkable for long, so that they must be taken immediately after preparing the aqueous suspension. This is because, after suspension in water, these products form a gel after only a few minutes and produce a thick, undrinkable agglomerate on the surface. In addition, with most of the products there is very rapidly at least a two-layer phase separation which no longer ensures homogeneous distribution of the active components in the stirred product. These products must also be taken with copious water because, otherwise, there is a risk of the possible formation of swollen agglomerates which, in the worst cases, may lead to blockage of the esophagus or else even of the gastrointestinal tract. Further disadvantages of these products are also the insipid taste and the artificial appearance.

In addition, DE 103 46 083 A1, which derives from the applicant, and the parallel documents belonging to the same patent family, WO 2005/027948 A1 and US 2005/0053676 A1, describe a laxative based on a powdered composition which, besides *plantago* seeds (plantaginis ovatae semen) and/or *plantago* seed husks and at least one anthranoid compound with a cathartic effect, in particular at least one sennoside, preferably in the form of anthranoid- or sennoside-containing plant constituents/parts, also comprises at least one polygalactomannan-based polysaccharide or derivative thereof, in particular guaran (guar gum). The latter acts firstly as (co)stabilizer in an aqueous suspension of the powdered composition, and secondly cooperates, especially because of its swelling ability, synergistically with the other components of the composition by assisting the cathartic effect thereof, and additionally facilitates the processability of the composition of the invention to a fine-particle powder which can be directly dispersed in water. However, an additional component, namely the polygalactomannan-based polysaccharide or derivative thereof, is necessary in the aforementioned composition in order to achieve the desired properties. It is also possible in some cases to employ relatively high dosages. Moreover, the aforementioned composition by its nature as a powder is associated with a high dust content.

U.S. Pat. No. 4,511,561 A which likewise derives from the applicant describes a laxative in the form of granules which, besides *plantago* seeds (plantaginis ovatae semen) and/or *plantago* seed husks and senna fruits, also comprises gum tragacanth.

PROBLEM TO BE SOLVED BY THE PRESENT INVENTION

Thus, the problem addressed by the present invention is to provide a composition for use as laxative which at least substantially avoids the aforementioned disadvantages.

A further problem of the present invention is to provide a composition which can be used as laxative and which on the one hand shows a good cathartic effect but, at the same time, also makes it possible for administration to be facilitated and free of complications, in particular without the previously described problems and risks.

DESCRIPTION OF THE PRESENT INVENTION

The applicant has now surprisingly found that the problem described previously can be solved by firstly providing the constituents of the senna fruits in the form of a senna fruit dry extract, and secondly dispensing with the incorporation of *plantago* seed husks, and employing exclusively *plantago* seed itself.

The present invention thus relates—according to a first aspect of the present invention—to a pharmaceutical composition which is suitable in particular for use as purgative (cathartic), where the composition comprises in combination and in each case in pharmaceutically effective amounts:
(A) senna fruit dry extract;
(B) *plantago* seed (plaginis ovatae semen).

The pharmaceutical composition of the invention shows by comparison with prior art compositions which employ dried and comminuted senna fruit themselves, as a result of the use of a senna fruit dry extract, an improved pharmacological and pharmaceutical activity with the same dosage amounts because of an increased active ingredient concentration in the senna fruit dry extract (i.e. concentration of hydroxyanthracene derivatives, especially sennosides).

As a result of the administration of intake quantities which are reduced compared with the prior art, the risk of the formation of swollen agglomerates which, in the worst cases, may lead to blockage of the esophagus or else even of the gastrointestinal tract, even on inappropriate use (especially on administration with amounts of liquid which are too small or even without amounts of liquid), is at least substantially precluded.

In addition, the pharmaceutical composition of the invention even without the presence of an additional (co)stabilizer is stably suspendable or dispersible or soluble in water, and an aqueous suspension of the composition of the invention remains stable and thus drinkable over a lengthy period, i.e. the suspension leads to no premature phase separation, nor does it prematurely form a gel. As a result of the dispensing with *plantago* seed husks, the suspendability or dispersibility is additionally improved and the problem and/or the risk of agglomerate formation is additionally reduced. For purposes of this application, standard conditions for dissolution include a ratio of about 1 g of the laxative composition to about 40 mL of water, at room temperature.

In order to obtain a good active ingredient concentration, the senna fruit dry extract employed according to the invention normally comprises a content of hydroxyanthracene derivatives, based on the senna fruit dry extract, and in particular calculated as sennoside B, of at least 3% by weight, in particular at least 5% by weight, preferably at least 7% by weight, particularly preferably at least 8% by weight. It may nevertheless be necessary in individual cases or on the basis of the application to deviate from the aforementioned contents of hydroxyanthracene derivatives, especially sennosides, without departing from the scope of the present invention.

All the weight data mentioned above and hereinafter are in each case based on the dry weight of the complete composition of the invention, unless the contrary is expressly noted.

The senna fruit dry extract employed according to the invention normally comprises a content of hydroxyanthracene derivatives, especially sennosides, based on the senna fruit dry extract and in particular calculated as sennoside B, in the range from 3 to 30% by weight, in particular 5 to 25% by weight, preferably 7 to 20% by weight, particularly preferably 8 to 15% by weight, very particularly preferably 8 to 12% by weight.

The drug/extract ratio of the senna fruit dry extract employed can vary within relatively wide ranges: normally, the senna fruit dry extract used according to the invention has a drug/extract ratio of at least 2:1, in particular at least 2.5:1, preferably at least 3:1. The drug/extract ratio of the senna fruit dry extract employed is generally in the range from 2:1 to 10:1, in particular 2.5:1 to 8:1, preferably 3:1 to 6:1. It may nevertheless be necessary in individual cases or based on the application to deviate from the aforementioned values without departing from the scope of the present invention.

Particularly good results are achieved when the senna fruit dry extract is based on fruits of the Alexandria senna plant and/or of the Tinnevelly senna plant, it being possible also to employ mixtures of the two aforementioned senna plants in any mixing ratios. The senna fruit dry extract employed according to the invention is normally obtainable by extracting fruits of the Alexandria senna plant and/or of the Tinnevelly senna plant. Details will be given in this regard about the extraction method in this regard, so that statements in this regard are unnecessary at this point.

The senna fruit dry extract employed according to the invention is advantageously designed to be soluble in water. This facilitates administration, because the senna fruit dry extract goes into solution on stirring with water and remains stable therein.

The senna fruit dry extract employed according to the invention generally comprises a mixture of different anthranoid compounds based on hydroxyanthracene derivatives, especially sennosides.

These hydroxyanthracene derivatives, in particular sennosides, are normally selected from the group of the following compounds of the general formula (I):

where in the general formula (I)
- the radical $R^1$ is hydrogen or a —CO—CO$_2$H group,
- the radical $R^2$ is a —CO$_2$H or —CH$_2$OH group, but with the proviso that when $R^1$ is a —CO—CO$_2$H group then $R^2$ is a —CO$_2$H group,
- the carbon atoms identified by the sign "*" in position 9 and 9' of the anthrone structure represent chirality centers, and mixtures and/or stereoisomers thereof, especially enantiomers and/or diastereoisomers, and/or derivatives of the aforementioned compounds.

In an embodiment which is preferred according to the invention, the hydroxyanthracene derivatives, in particular sennosides, are selected from the group of the following compounds of the general formula (I) and mixtures thereof:

| Compound | $R^1$ | $R^2$ | 9-9' |
|---|---|---|---|
| (I A) | —H | —CO$_2$H | R*,R* (threo) |
| (I B) | —H | —CO$_2$H | R*,S* (erythro) |
| (I C) | —H | —CH$_2$OH | R*,R* (threo) |
| (I D) | —H | —CH$_2$OH | R*,S* (erythro) |
| (I E) | —CO—CO$_2$H | —CO$_2$H | R*,R* (threo) |
| (I F) | —CO—CO$_2$H | —CO$_2$H | R*,S* (erythro) |

For achieving a good pharmaceutical or pharmacological effect, it is advantageous for the pharmaceutical composition of the invention to comprise the senna fruit dry extract in amounts of at least 1% by weight, in particular at least 2% by weight, preferably at least 3% by weight, particularly preferably at least 4% by weight, very particularly preferably at least 5% by weight, based on the composition. The pharmaceutical composition of the invention generally comprises the senna fruit dry extract in amounts of from 1 to 15% by weight, in particular 2 to 10% by weight, preferably 3 to 8% by weight, particularly preferably 4 to 7% by weight, very particularly preferably 4.5 to 6.5% by weight, based on the composition. It may nevertheless be necessary in individual cases or based on the application to deviate from the aforementioned amounts without departing from the scope of the present invention.

The pharmaceutical composition of the invention generally has a total content of hydroxyanthracene derivatives, in particular sennosides, of at least 0.1% by weight, in particular at least 0.2% by weight, preferably at least 0.3% by weight, particularly preferably at least 0.4% by weight, very particularly preferably at least 0.5% by weight, based on the composition and in particular calculated as sennoside B. The total content of hydroxyanthracene derivatives, in particular sennosides, in the composition of the invention, based on the composition and in particular calculated as sennoside B, is normally from 0.1 to 2% by weight, in particular 0.2 to 1% by weight, preferably 0.3 to 0.8% by weight, particularly preferably 0.4 to 0.7% by weight. It may nevertheless be advantageous or necessary in individual cases or based on the application to deviate from the aforementioned amounts without departing from the scope of the present invention.

In relation to the *plantago* seed component in the composition of the invention, the content thereof ought to be, to achieve a good activity, at least 20% by weight, in particular at least 30% by weight, preferably at least 40% by weight, particularly preferably at least 50% by weight, very particularly preferably at least 60% by weight, based on the composition. The *plantago* seed content in the composition of the invention is normally in the range from 20 to 90% by weight, in particular 30 to 90% by weight, preferably 40 to 85% by weight, particularly preferably 50 to 80% by weight, very particularly preferably 65 to 75% by weight. However, it may be necessary in individual cases or based on the application to deviate from the aforementioned amounts without departing from the scope of the present invention.

The pharmaceutical composition of the invention is advantageously in the form of granules. A number of advantages are associated therewith. The granule form facilitates administration in several ways: firstly, dosage is facilitated (e.g. the granule form makes teaspoon dosage possible), and secondly the granule form increases on the one hand the storage stability of the composition, and on the other hand its suspendability or solubility in water for the relevant administration (i.e. stated more accurately the psyllium seed constituents go into suspension, while the other constituents, especially the senna fruit dry extract and, where appropriate, further ingredients such as, for example, granule formers, go into solution). It is also possible in this way to increase the stability of the prepared suspension or solution. In addition, the granule form ensures that the composition of the invention is dust-free, which facilitates in particular the usability and minimizes the risks (e.g. inhalation on inappropriate use) connected therewith.

It was not to be expected by the skilled worker that the composition of the invention can in fact be processed to granules, because relevant attempts with comminuted constituents of senna fruits and psyllium constituents lead to agglomerations and premature swelling. Only through the use of the senna fruit dry extract is it possible to convert the composition of the invention into granule form, which was not predictable in advance.

If the pharmaceutical composition according to the present invention is in granule form, it normally comprises in addition (C) at least one granule former. The granule former—also referred to synonymously as granulation aid, granulating substance etc.—serves to a certain extent as matrix substance or, as it were, as "adhesive" for the ingredients to be granulated. Concerning this, details will be given below within the framework of the description of the manufacturing method of the invention, so that further statements are unnecessary at this point.

The amount of granule former employed in the pharmaceutical composition of the invention can vary within wide limits. In the case of granules, the pharmaceutical composition according to the invention normally comprises the granule former(s) in amounts of from 3 to 30% by weight, in particular 4 to 25% by weight, preferably 5 to 20% by weight, particularly preferably 6 to 15% by weight, very particularly preferably 7 to 10% by weight, based on the composition. Nevertheless, it may be necessary or advantageous in individual cases or based on the application to deviate from the aforementioned quantitative data without departing from the scope of the present invention.

Granule formers suitable for this purpose are known as such to the skilled worker. For example, the granule former employed according to the invention can be selected from the group of starch derivatives (e.g. starch degradation products, especially dextrins and maltodextrins, preferably maltodextrins), cellulose and cellulose derivatives (e.g. ethylcellulose), poly(meth)acrylic acids and poly(meth)acrylates (e.g. Eudragits® or carbomers, such as, for example, Carbopol®), gelatin, polyvinylpyrrolidone (PVP), polyalkylene glycols (e.g. polyethylene glycol such as, for example, Movicol®), dextrose (D-glucose), lactose, maltose and sugar substitutes (e.g. fructose and sugar alcohols such as, for example, mannitol, xylitol, sorbitol (D-glucitol), isomaltitol (isomalt), maltitol and lactitol), and mixtures thereof.

Particularly preferred granule formers are starch derivatives, especially starch degradation products such as, in particular, dextrins and maltodextrins, particularly preferably maltodextrins. For further details concerning dextrins and maltodextrins, reference may be made in particular to Römpp Chemie-Lexikon [Römpp's Encyclopedia of Chemistry], 10th edition, Georg Thieme Verlag Stuttgart/New York, Volume 2, 1997, page 928, entry: "Dextrine [dextrines]", and Volume 4, 1998, page 2513, entry: "Maltodextrine [maltodextrines]", and to Römpp Lexikon Lebensmittelchemie [Römpp's Encyclopedia of Food Chemistry], Georg Thieme Verlag Stuttgart/New York, 9th edition, 1995, page 213, entry: "Dextrine [dextrines]", and page 518, entry: "Maltodextrine [maltodextrines]", and the literature referred to therein in each case, the respective content of which is hereby incorporated by reference.

The granule former employed according to the invention should advantageously be water-soluble or at least water-dispersible, preferably water-soluble, in order on the one hand to be able to be sprayed as solution in the granulation, and on the other hand in order to be soluble in the drinking liquid on oral administration with water.

Granule formers which have proved to be particularly suitable are maltodextrins. Maltodextrins are suitable as particularly stable matrix substances for building up the granules and ensure good adhesion or bonding of the individual ingredients and are additionally suitable in the preparation and administration because they ensure in particular an especially good and rapid solubility or suspendability of the corresponding drinking liquid, especially also in the cold state.

As outlined above and will be described below in the framework of the manufacturing method of the invention, in the case where the composition of the invention is configured as granules, the granules are advantageously obtainable by fluidized bed granulation.

Besides the aforementioned active and other ingredients, the composition of the invention may additionally comprise at least one further additive, at least one further ingredient and/or one further added substance. The latter can be selected in particular from the group of colorants such as natural or nature-identical colorants, flavorings, flavor enhancers and aromatizing agents, sweeteners, acidifiers, preservatives, stabilizers and costabilizers, electrolytes, minerals and mineral substances, vitamins, fillers, flow agents and processing aids, and mixtures of the aforementioned compounds.

The pharmaceutical composition according to the invention, in particular in the form of granules, advantageously has a defined particle size and/or a defined particle size distribution. The particle sizes can be determined by methods known per se, e.g. by sieve analysis, granulometry, by light diffraction, microscopy etc. The following particle size data and particle size distribution data relate in particular to values from sieve analysis according to Ph. Eur. (Pharmacopoea Europea), 5th edition, Principal Volume 2005, page 298, section 2.9.12 "Sieve analysis [Siebanalyse]" (ISBN No. 3-7692-3638-6).

The pharmaceutical composition according to the present invention, in particular in the form of granules, is generally at least substantially dust-free. This has not only advantages for manufacturing techniques, but also advantages in relation to use, because no agglomeration occurs when the composition of the invention is stirred into the drinking liquid and, moreover, inhalation is precluded even on inappropriate administration, and no premature swelling of the *plantago* seed takes place in the stored state.

Normally, the pharmaceutical composition according to the present invention, in particular in the form of granules, has an average particle size in the range from 50 to 400 µm, in particular 50 to 300 µm, preferably 75 to 275 µm. On the one hand, this enables problem-free manufacture and, on the other hand, this leads to good storage stability and to good stirrability into the administration liquid.

In a preferred embodiment, the chief mass fraction of the pharmaceutical composition according to the present invention (in particular in the form of granules), preferably more than 55% by weight, in particular more than 60% by weight, or preferably more than 65% by weight, particularly preferably more than 70% by weight, very particularly preferably more than 75% by weight of the particles of the composition has particle sizes in the range from 50 to 1000 µm, preferably with a maximum of the distribution in particular at particle sizes in the range from 65 to 500 µm, preferably 125 to 450 µm.

In an embodiment which is particularly preferred according to the invention, the pharmaceutical composition according to the present invention, in particular in the form of granules, has the following particle size distribution:

more than 99% by weight, preferably 100% by weight, of the particles of the composition smaller than 2000 µm; and/or more than 94% by weight, in particular more than 95% by weight, preferably more than 96% by weight, of the particles of the composition smaller than 1000 µm; and/or more than 50% by weight, in particular more than 55% by weight, preferably more than 60% by weight, particularly preferably more than 65% by weight, very particularly preferably more than 70% by weight, of the particles of the composition smaller than 500 µm; and/or less than 10% by weight, in particular less than 5% by weight, preferably less than 4% by weight, particularly preferably less than 3% by weight, very particularly preferably less than 1% by weight, of the particles of the composition smaller than 63 µm;

where all the aforementioned weight data are in each case based on the dry weight of the complete composition.

In an embodiment which is very particularly preferred according to the invention, the pharmaceutical composition according to the present invention, in particular in the form of granules, has the following particle size distribution (sieve spectrum according to sieve analysis):

particle sizes>2000 µm:

less than 1% by weight, in particular 0% by weight;

2000 µm≦particle sizes>1000 µm:

0.5 to 10% by weight, in particular 1 to 10% by weight, preferably 1 to 6% by weight;

1000 µm≦particle sizes>500 µm:

15 to 45% by weight, in particular 20 to 40% by weight, preferably 25 to 40% by weight;

500 µm≦particle sizes>250 µm:

35 to 60% by weight, in particular 40 to 55% by weight, preferably 40 to 50% by weight;

250 µm≦particle sizes>125 µm:

5 to 30% by weight, in particular 10 to 25% by weight, preferably 10 to 20% by weight;

125 µm≦particle sizes>63 µm:

0.5 to 5% by weight, in particular 0.5 to 4% by weight, preferably 1 to 3% by weight;

63 µm≦particle sizes>45 µm:

0 to 3% by weight, in particular 0 to 1% by weight, preferably 0% by weight;

where all the aforementioned weight data are in each case based on the dry weight of the complete composition, and with the proviso that the total of the percent by weight data is 100% by weight (i.e. the weight fractions of the particles with the individual particle size ranges are to be combined in such a way that the total is 100% by weight).

In addition, the pharmaceutical composition according to the present invention advantageously has a bulk density in the range from 250 to 650 g/l, in particular 300 to 600 g/l, preferably 350 to 550 g/l, particularly preferably 400 to 500 g/l. This makes it possible for the pharmaceutical composition of the invention, advantageously in the form of granules, to be dosed satisfactorily, in particular by teaspoon.

Thus, in the context of the present invention there is provision of a pharmaceutical composition, in particular in the form of granules, which avoids or else at least diminishes in an efficient manner the prior art disadvantages outlined at the outset.

The use of a senna fruit dry extract achieves, by comparison with the prior art, a significantly higher hydroxyanthracene derivative content, in particular sennoside content, for the same dosage quantity, leading to the advantage that smaller amounts of the composition need to be administered than in the prior art to achieve a comparable effect, and this is not only desirable from the physiological viewpoint, but also minimizes the risk of hazards on inappropriate use (e.g. no risk of agglomeration if taken with too little liquid etc.). The use of a senna fruit dry extract also has a number of advantages for the techniques of manufacture and use: the use of a senna fruit dry extract distinctly facilitates the manufacture of the complete composition; the senna fruit dry extract can in particular be granulated better and more storage-stably than the dried and comminuted senna fruits. A further advantage of the use of the senna fruit dry extract, in particular in the context of the composition of the invention in the form of granules, is the improved solubility or suspendability on oral use; in particular, the pharmaceutical composition can be converted into a stable suspension or solution whose consistency is substantially unchanged over several hours and thus remains ready for use over several hours. Thus, the senna fruit dry extract employed according to the invention is water-soluble. As a result of the composition of the invention being dust-free there are associated advantages for the technique of manufacture and in relation to use.

The result is that it is possible in the context of the present invention to provide a pharmaceutical composition which is distinctly improved compared with the prior art.

The present invention relates—according to a second aspect of the present invention to a method for manufacturing the previously described pharmaceutical composition according to the present invention. In the manufacturing method of the invention, the previously defined active and/or other ingredients of the composition of the invention, in particular (A) the senna fruit dry extract and (B) the *plantago* seed (plantaginis ovatae semen) and, where appropriate, further constituents of the composition as have been defined previously, where appropriate after previous adjustment of the particle sizes, in particular by means of comminution, are subjected to a granulation, preferably in a fluidized-bed method, in the presence of (C) at least one previously defined granule former. Concerning the proportionate amounts and concentrations of the individual active and/or other ingredients, reference may be made to the preceding statements concerning the composition of the invention, which apply correspondingly in relation to the manufacturing method of the invention, so that unnecessary repetitions are superfluous. The granulation is normally additionally carried in the presence of a granulating liquid, generally water; as known as such to the skilled worker, the granulating liquid is introduced with a particular spraying rate, as will be described below.

The procedure for this is normally such that initially a powdered mixture of the active and other ingredients of the composition of the invention is prepared, it being advantageous for the particle sizes to be adjusted appropriately for the subsequent granulation. Advantageously, the particle sizes in the initial powdered mixture are adjusted to below 200 μm, preferably below 150 μm. Subsequently, the powdered mixture is then granulated, preferably by fluidized-bed granulation, normally fluidizing with an inlet air rate, in particular a machine-dependent inlet air rate, of about 200 to 300 m³/h and, after a suitable inlet air temperature has been reached, starting with the spraying in of the moisture, especially water or water vapor. It is possible in principle for all the active and/or other ingredients of the composition of the invention to be introduced into the initial mixture in powder form. It is also possible alternatively—and this is preferred according to the invention—to introduce only part of the active and other ingredients, generally at least the senna fruit dry extract and the comminutated *plantago* seeds, into the mixture in powder form, but to dissolve other constituents or ingredients, especially those soluble in water in the granulating liquid and combine them with the other constituents to give the relevant granules only during the granulation process.

Thus, to carry out an efficient granulation, the granulation is carried out in the presence of at least one previously defined granule former, i.e. normally the granule former is already present in the initial mixture in powder form, or else is—in a manner which is preferred according to the invention—dissolved in the granulating liquid to be introduced.

The granulation generally takes place with a suitable spraying rate (ml/min), e.g. with an average set spraying rate of from 10 to 100 ml of granulating liquid per minute, and/or over a granulation time totaling from 30 to 300 minutes and/or at a granulation temperature in the range from 30 to 150° C., in particular 30 to 100° C. (e.g. machine-dependently for example also temperatures where appropriate different therefrom, in particular higher).

It is possible by adjusting or controlling the previously described granulation conditions, and by granulometry of the initial particles to control deliberately in an efficient manner the particle sizes and particle size distribution of the final product or of the granules, and to adjust the desired granulometry as defined above.

For further details of granulation methods, in particular fluidized-bed method, it is possible in general to refer to the general specialist literature, for example to Römpp Chemie-Lexikon, Georg Thieme Verlag Stuttgart/New York, 10th edition, e.g. the entries: "Granulate [granulates]", "Prillen [prilling]" and "Wirbelschichtverfahren [fluidized bed processes]", and the literature cited therein.

It is completely surprising that the composition of the invention can be converted in the manner described above into granules, because it would in principle have been expected that the *plantago* seed would agglomerate and swell prematurely. Surprisingly, however, these phenomena do not occur under the aforementioned granulation conditions, and granules can be produced in an efficient manner.

Figure 6:
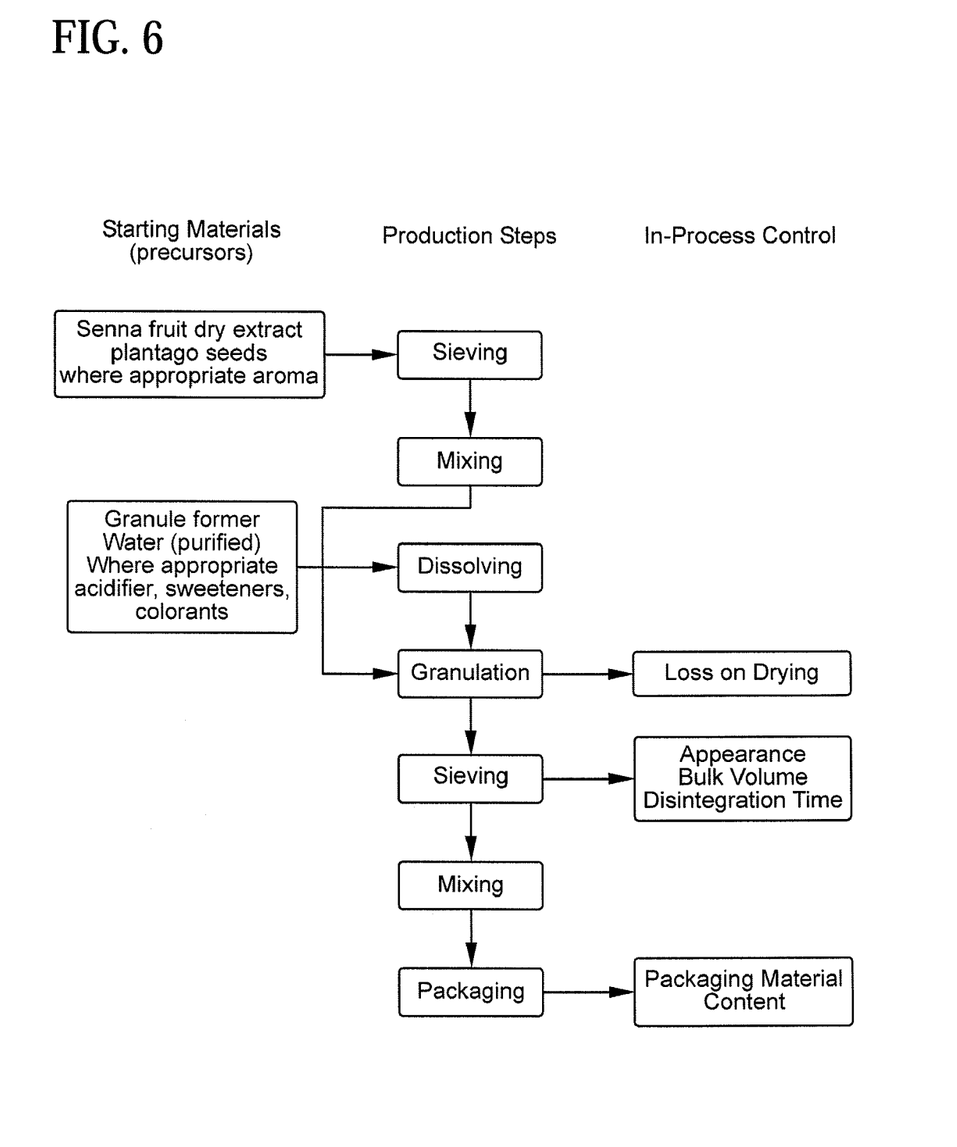
FIG. 6 shows a flow diagram of the method of the invention in a typical embodiment.

FIG. 6 shows in the form of a flow diagram in a diagrammatic overview of the method of the invention in a typical embodiment as has been described above and will also be represented below in the exemplary embodiments.

Figure 5:
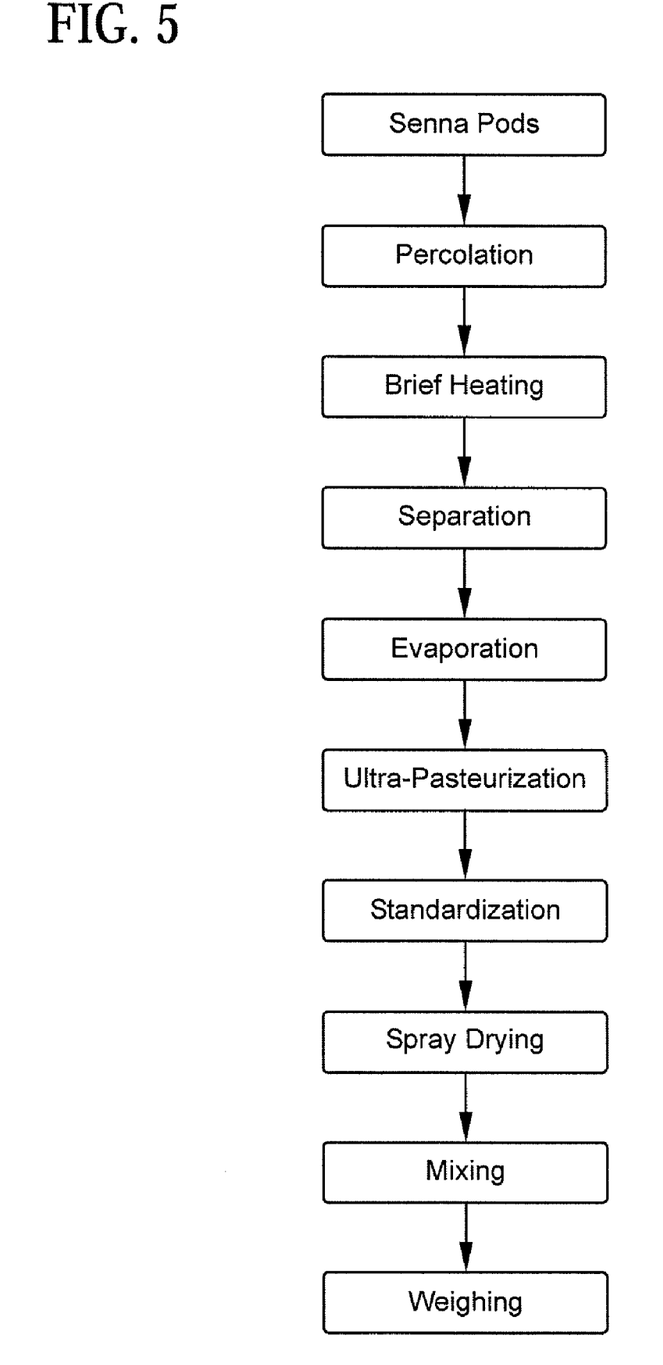
FIG. 5 shows a flow diagram of the process for producing the senna fruit dry extract in a typical embodiment.

The senna fruit dry extract—also referred to synonymously as senna pod dry extract employed according to the invention is generally produced by transferring suitably comminuted senna pods or senna fruits based on Alexandria senna fruits and/or Tinnevelly senna fruits (either one variety in each case or in any mixing ratio) into percolators which are filled with cold water, connected in series and percolated upward. The percolate is subsequently collected in a dilute extract container and then heated by brief heating. The precipitated solids are removed in a separator. The dilute extract is concentrated with the aid of a vacuum falling-film evaporator. The concentrated extract is then ultra-pasteurized in an ultra-pasteurization system. The spray solution is then mixed with carbon dioxide and dried in a spray tower. The sprayed product is mixed in a mixer, in particular in an orbiting screw mixer, and—where appropriate after intermediate storage—passed on for subsequent manufacture of the composition of the invention. The senna fruit dry extract employed according to the invention is soluble in water. A diagrammatic overview of the process for producing the senna fruit dry extract is depicted in FIG. 5.

For further details of the manufacturing method of the invention, reference may be made to the exemplary embodiments.

As described above, the composition according to the present invention is suitable in particular for use as laxative (cathartic, purgative).

The present invention thus relates—according to a third aspect of the present invention—to the use of the pharmaceutical composition described above as laxative (purgative, cathartic) and to the use of the pharmaceutical composition according to the present invention described above for the manufacture of a medicament or of a pharmaceutical composition for promoting and/or facilitating and/or regulating bowel evacuation and/or bowel activity.

In the context of the use according to the invention, the pharmaceutical composition according to the present invention can be employed in particular for the prophylactic or curative treatment of disorders in which easy defecation with light stool, in particular for hemorrhoidal disorders, conditions following rectal/anal surgical procedures and before and after surgical procedures on the abdominal cavity, and for constipation, or for facilitating passage through the bowel and defecation, in particular for alleviating the side effects of therapy with constipation-causing medicaments.

In the context of the use according to the invention, the composition of the invention is taken orally, preferably as aqueous suspension or solution, in particular in single doses of from 1 to 5 g, in particular 2 to 4 g, preferably 2.5 to 3.5 g. Normal daily doses are in the range of in total from 1 to 50 g, preferably 1 to 20 g, particularly preferably 3 to 10 g, of the composition of the invention. As a result of the provision of the sennosides in the form of a senna fruit dry extract, it is possible in the context of the composition of the invention to reduce significantly, normally by up to 50% or even more, both the single doses and the daily doses by comparison with prior art compositions which employ dried and powdered senna fruits.

The composition of the invention can, for the purposes of simplified administration, be provided in pack units (e.g. sachets) for the appropriate single doses (e.g. sachets containing 1 to 5 g). Because the composition of the invention, in particular in the form of granules, is easily meterable, the composition of the invention can, however, also be provided in large containers (e.g. cans with 40 to 1000 g) because it is possible with the composition of the invention easily to use a teaspoon for dosage.

The present invention further relates—according to a fourth aspect of the present invention—to a method for treating the human body, in particular for the purposes of prophylactic or curative treatment of disorders and conditions of the aforementioned type, where in the context of the method of the invention a pharmaceutically or pharmacologically effective amount of the composition according to the present invention described above is administered, preferably orally, in particular in the form of an aqueous suspension or solution.

For further details of the use according to the invention and of the treatment method according to the invention, reference may be made, to avoid unnecessary repetitions, to the statements above concerning the pharmaceutical composition of the invention, which apply correspondingly in relation to the use according to the invention and the treatment method according to the invention.

Further refinements, modifications and variations of the present invention will be directly evident and achievable for a skilled worker reading the description without departing from the scope of the present invention.

The present invention is illustrated by means of the following exemplary embodiments which do not, however, restrict the present invention in any way.

WORKING EXAMPLE OF THE PRESENT INVENTION

Manufacture of Pharmaceutical Compositions of the Invention for Use as Purgatives The following weights were chosen to manufacture a composition of the invention:

| | |
|---|---:|
| Senna fruit dry extract (10%) | 506.67 g |
| Plantago seeds (maximum particle size: 140 µm) | 7,000 g |
| Colorant | 76 g |
| Aromatizing substance | 400 g |
| Sweetener | 28 g |
| Granule former (maltodextrin) | 836 g |
| Acidifier (citric acid, anhydrous) | 1,153 g |
| Water (granulating liquid) | 4 kg |

A powdered mixture was produced from the *plantago* seeds, the senna fruit dry extract and the aromatizing substance. The other raw materials were dissolved in water; the solution was clear and was subsequently used as granulating liquid.

A fluidized-bed granulation was subsequently carried out. For this purpose, the powdered mixture was transferred into the fixed-bed granulation. 200 to 300 m$^3$/h was used for fluidization. After the inlet air temperature reached 70° C., spraying was started. The inlet air temperature rose during the process up to 85° C. The product temperature was up to 60° C. at intermediate times, averaging 40 to 50° C. The granulation took place with an average adjusted spraying rate of 46 ml/min, equivalent to an actual spraying rate of 29.7 g of granulating liquid/minute. The total time was 145 minutes. The resulting granules were dried for about 1 hour until the loss on drying was less than 5%. The maximum product temperature was 60° C. The yield was 8 kg.

Figure 1:
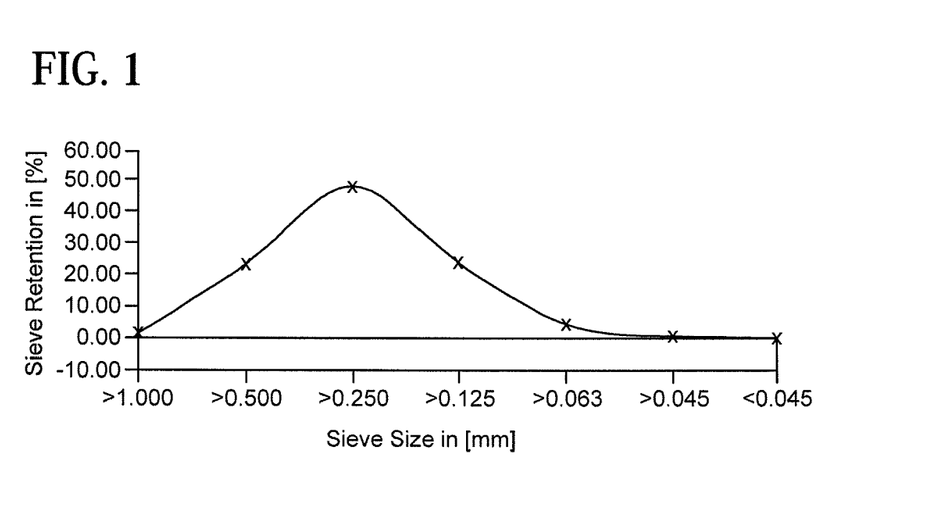
FIG. 1 shows the particle size distribution of the granules in one embodiment of the present invention.

The particle size distribution of the resulting granules is shown in FIG. 1.

Figure 2:
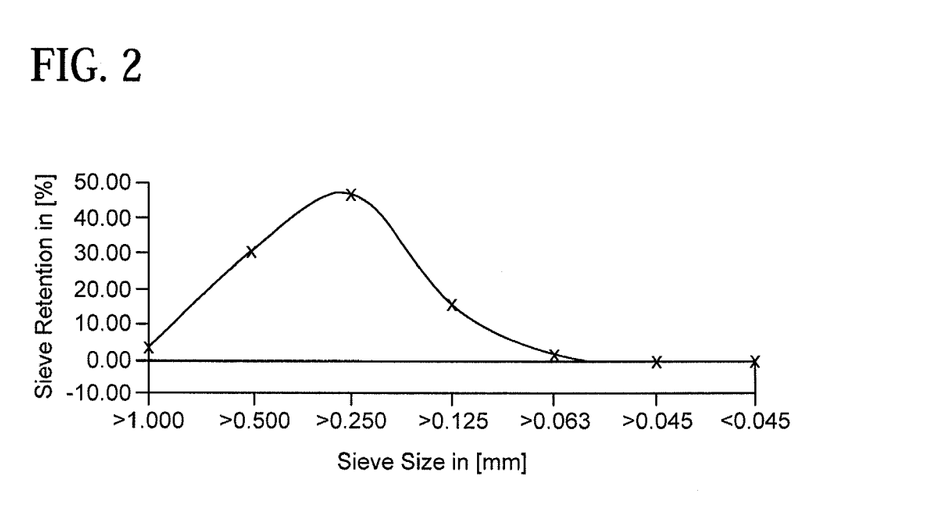
FIG. 2 shows the particle size distribution of the granules in a second embodiment of the present invention.
Figure 3:
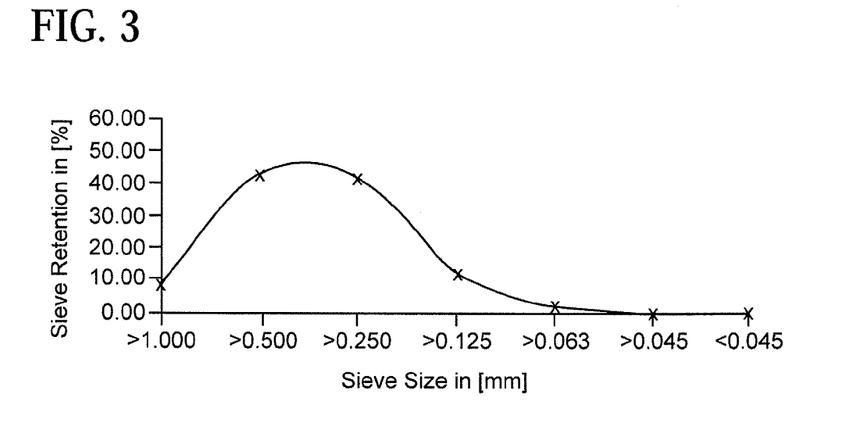
FIG. 3 shows the particle size distribution of the granules in a third embodiment of the present invention.
Figure 4:
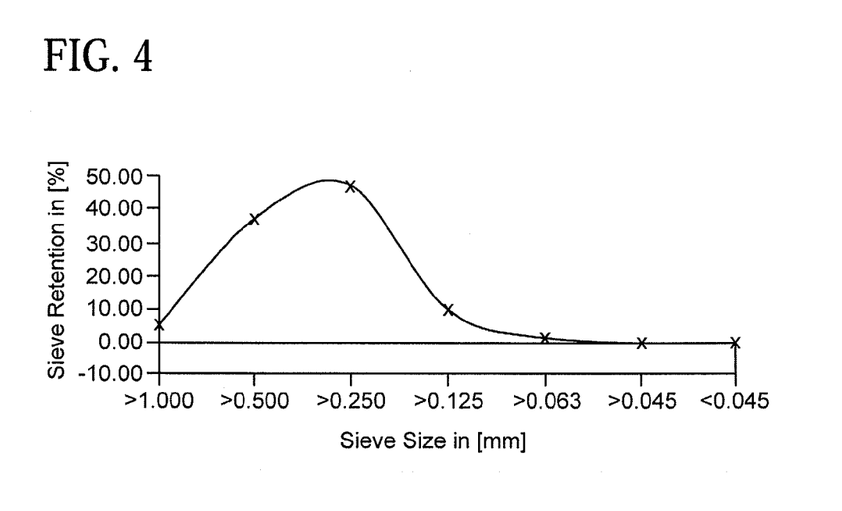
FIG. 4 shows the particle size distribution of the granules in a fourth embodiment of the present invention.

The previously described mode of manufacture was repeated to manufacture three further compositions of the invention with variation of the granulation conditions. The corresponding particle size distributions of the resulting granules are shown in FIGS. 2 to 4.

Compositions of the invention with different flavors were also produced in a corresponding manner (e.g. apple and cherry).

The senna fruit dry extract employed according to the invention was produced as follows: the suitable comminuted senna fruits were put into percolators; the percolators were filled with cold water, connected in series and percolated upward. The percolate was then collected in the dilute extract container and subsequently heated by brief heating. The precipitated solids were removed in a separator, and the dilute extract was concentrated using a vacuum falling-film evaporator, and the concentrated extract was subsequently ultra-pasteurized in an ultra-pasteurization system. For quality control, samples were taken to determine the dry matter content. This was followed by spray drying in a spray tower, with carbon dioxide having been added to the spray solution. Finally, the sprayed product was mixed in an orbiting screw mixer, the mixture was weighed and put into temporary packages until employed in the manufacturing method of the invention. The weight per liter of the senna fruit dry extract produced in this way was in the range from 100 to 300 g/l, and the bulk density was in the range from 200 to 400 g/l. The initial senna fruit mixture employed was a 50:50 mixture of Alexandria senna fruits and Tinnevelly senna fruits. The resulting senna fruit dry extract had a content of hydroxyanthracine derivatives, calculated as sennoside B and based on the senna fruit dry extract, of 10%.

Preparation of Aqueous Suspensions for Oral Administration

A composition of the invention manufactured as above, and two prior art comparative products, are converted into an aqueous suspension. For this purpose, in each case 5 g of the compositions are stirred into portions of about 200 ml of tap water.

The first comparative composition is a powdery commercial product based on Indian plantain husks (psyllium) which comprises in addition further ingredients (inter alia natural and synthetic colorants, flavorings, aromatizing agents and sweeteners, citric acid, iron oxide and calcium) but is free of sennosides.

The second comparative composition is a powdery composition in the form of a fine-particle powder (more than 70% by weight of the particles with average diameters in the range from 125 to 250 µm) which comprises 52% by weight *plantago* seeds, 2.2% by weight *plantago* seed husks, 12.3% by weight Tinnevelly senna fruits and Alexandria senna fruits (mixing ratio=1:1), equivalent to about 0.3% by weight sennosides, 8.3% by weight guar gum, 0.07% by weight fine-particle silica, 0.03% by weight maltodextrin and 25.1% by weight further ingredients (i.e. natural aromatizing substances, colorants, flavorings and sweeteners).

After the three compositions have been suspended in water, only the composition of the invention and the second comparative composition, which corresponds to the applicant's own DE 103 46 083 A1, remain stable for more than a quarter of an hour, whereas the comparative suspension with the first comparative composition shows phase separation after only a few minutes and, after a quarter of an hour, has formed a gel and a thick, undrinkable agglomerate on the surface; in addition, the first comparative composition also shows disadvantages through its insipid taste and artificial appearance.

After a further three hours, however, the aqueous suspension with the second comparative composition according to DE 103 46 083 A1 also showed phase separation, whereas the aqueous suspension with the composition of the invention still showed no phase separation and moreover remained phase-stable and drinkable for several hours more.

In addition, the aforementioned three compositions differ significantly in their laxative effect. Whereas the first comparative composition based on Indian plantain husks (psyl-lium) shows only a moderate cathartic effect, which is not always adequate in severe cases of constipation, the second comparative composition shows a distinctly better cathartic effect because of the combination of physical effect of the *plantago* seeds/*plantago* seed husks as a result of swelling on the one hand and pharmacologically stimulating action of the sennosides on the other hand, although accurate dosage with a teaspoon is not possible owing to the mixture being in powder form, and on the other hand the danger of risks (e.g. agglomeration) cannot be precluded on inappropriate administration.

Only with the composition of the invention is dosage with a teaspoon possible, because of the granule form, and premature agglomeration even on inappropriate use is at least substantially precluded; in addition, as a result of the use of senna fruit dry extract the concentration of sennosides is increased to such an extent that a distinctly smaller amount is needed to be taken (specifically about one half) to achieve a comparable laxative effect, thus further minimizing the risk even on inappropriate use.

As a result, it has been possible in the context of the present invention to provide an efficient pharmaceutical composition for use as laxative which efficiently avoids the prior art disadvantages described at the outset.

What is claimed is:

1. A pharmaceutical composition for use as a purgative, where the composition comprises in combination and in each case in pharmaceutically effective amounts:
    a) a dried aqueous extract of senna fruit; and
    b) *plantago* seeds (plantaginis ovatae semen),
wherein the combination, when combined with water, is non-agglomerating under standard conditions.

2. The pharmaceutical composition of claim 1, where the dried aqueous extract of senna fruit comprises at least 3% by weight, based on the dried aqueous extract of senna fruit, of hydroxyanthracene derivatives, calculated as sennoside B.

3. The pharmaceutical composition of claim 1, where the dried aqueous extract of senna fruit comprises 3 to 30% by weight, based on the dried aqueous extract of senna fruit, of hydroxyanthracene derivatives, calculated as sennoside B.

4. The pharmaceutical composition of claim 1, where the dried aqueous extract of senna fruit comprises a drug/extract ratio of at least 2:1.

5. The pharmaceutical composition of claim 1, where the dried aqueous extract of senna fruit comprises fruit from the group of plants consisting of Alexandria senna plant, Tinnevelly senna plant, and mixtures thereof.

6. The pharmaceutical composition of claim 1, where the composition comprises at least 1%, by weight, of the dried aqueous extract of senna fruit.

7. The pharmaceutical composition of claim 1, where the composition comprises at least 0.1%, by weight, of sennoside hydroxyanthracene derivative.

8. The pharmaceutical composition of claim 1, comprising 20 to 90%, by weight, of the *plantago* seeds.

9. The pharmaceutical composition of claim 1 wherein the composition comprises particles, and wherein more than 55% of the particles have a particle size greater than 50 µm.

10. The pharmaceutical composition of claim 9 further comprising at least one granule former.

11. The pharmaceutical composition of claim 10, comprising 3 to 30%, by weight, based on the total composition weight of said granule former.

12. The pharmaceutical composition of claim 1 further comprising at least one member of the group consisting of colorants, flavorings, flavor enhancers and aromatizing agents, sweeteners, acidifiers, preservatives, stabilizers and costabilizers, electrolytes, minerals, mineral substances, vitamins, fillers, flow agents and processing aids, and mixtures of the aforementioned materials.

13. The pharmaceutical composition of claim 1 wherein the composition comprises particles having an average particle size in the range from 50 to 400 μm.

14. The pharmaceutical composition of claim 1, wherein the composition comprises particles, and wherein at least 55%, by weight, of the particles of the composition have a particle size in the range from 50 to 1000 μm, where the maximum distribution curve is at particle sizes in the range from 65 to 500 μm.

15. The pharmaceutical composition of claim 1, comprising particles having the following particle size distribution:
  a) more than 99%, by weight, of the particles of the composition have a size less than 2000 μm; and
  b) more than 94%, by weight, of the particles of the composition have a size less than 1000 μm; and
  c) more than 50%, by weight, of the particles of the composition have a size less than 500 μm; and
  d) fewer than 10%, by weight, of the particles of the composition have a size less than 63 μm;
  where all the aforementioned weight data are in each case based on the dry weight of the total composition.

16. The pharmaceutical composition of claim 1 having a bulk density in the range from 250 to 650 g/l.

17. A method for manufacturing a pharmaceutical composition for use as a purgative comprising:
  a) combining pharmaceutically effective amounts of a dried aqueous extract of senna fruit and *plantago* seeds (plantaginis ovatae semen); and
  b) granulating said pharmaceutical composition in the presence of at least one granule former to form granules, 99% of which have a particle size between 45 and 2000 μm.

18. A method for treating a mammal suffering from an obstipation, said method comprising: administering a pharmaceutically effective amount of a laxative composition, said laxative composition comprising in combination and in pharmaceutically effective amounts each
  a) a dried aqueous extract of senna fruit; and
  b) *plantago* seeds (plantaginis ovatae semen),
wherein the combination is non-agglomerating, when combined with water, under standard conditions.

19. The method of claim 18, where the laxative composition is administered orally.

20. The method of claim 18, where the laxative composition is administered as aqueous suspension or solution.

* * * * *